United States Patent [19]

Hara et al.

[11] Patent Number: 5,073,649

[45] Date of Patent: * Dec. 17, 1991

[54] PROCESS FOR PRODUCING A POLYALKYLENE POLYAMINE

[75] Inventors: Yasushi Hara; Nobumasa Suzuki, both of Shin-nanyo; Yukio Ito, Kudamatsu; Kazuhiko Sekizawa, Shin-nanyo, all of Japan

[73] Assignee: Tosoh Corporation, Shin-nanyo, Japan

[*] Notice: The portion of the term of this patent subsequent to Jan. 1, 2008 has been disclaimed.

[21] Appl. No.: 307,943

[22] Filed: Feb. 9, 1989

[30] Foreign Application Priority Data

Feb. 10, 1988 [JP] Japan .................................. 63-27489
Dec. 5, 1988 [JP] Japan ................................. 63-306150

[51] Int. Cl.$^5$ .......................................... C07C 209/00
[52] U.S. Cl. ................................... 564/479; 502/353; 564/480
[58] Field of Search ................. 564/479, 480; 544/358

[56] References Cited

U.S. PATENT DOCUMENTS

| 4,316,840 | 2/1982 | Ford et al. .......................... 540/474 |
| 4,337,175 | 6/1982 | Ramirez ............................... 502/340 |
| 4,463,193 | 7/1984 | Johnson et al. ..................... 564/479 |
| 4,550,209 | 10/1985 | Unvert et al. ....................... 564/479 |
| 4,683,335 | 7/1987 | Knifton et al. ...................... 564/380 |
| 4,906,782 | 3/1990 | Hara et al. .......................... 564/478 |

FOREIGN PATENT DOCUMENTS

| 230776 | 8/1987 | European Pat. Off. . |
| 256516 | 2/1988 | European Pat. Off. ............ 502/353 |
| 3543228 | 6/1986 | Fed. Rep. of Germany ...... 564/479 |
| 2147896 | 5/1985 | United Kingdom . |

OTHER PUBLICATIONS

Barnes et al., "Ethylenediamine by Low-Pressure Ammonolysis of Monoethanolamine", *Ind. Eng. Chem. Prod. Res. Dev.*, 1981, 20, pp. 399–407.
Patent Abstracts of Japan, vol. 11, No. 3 (C-395)[2450], 7th Jan. 1987; & JP-A-61 183 249 (Mitsui Toatsu Chem. Inc.) 15-08-1986 *Abstract*.

*Primary Examiner*—Glennon H. Hollrah
*Assistant Examiner*—Scott C. Rand
*Attorney, Agent, or Firm*—Oblon, Spivak, McClelland, Maier & Neustadt

[57] ABSTRACT

A process for producing an alkylenamine, which comprises reacting ammonia and/or a polyalkylene polyamine with an alkanolamine to obtain an alkylenamine having an increased number of alkylene chains over the ammonia and/or the alkylenamine as starting material, wherein a catalyst having a niobium-containing substance supported on a carrier is used for the reaction.

7 Claims, No Drawings

PROCESS FOR PRODUCING A POLYALKYLENE POLYAMINE

The present invention relates to a process for producing a polyalkylene polyamine. More particularly, it relates to a process for producing a polyalkylene polyamine using a catalyst having a niobium-containing substance supported on a catalyst.

As a process for producing polyalkylene polyamines, particularly ethylenamines which are particularly important from the industrial point of view, a process is known wherein ethylene dichloride is reacted with ammonia. By this process, the production of piperazine and piperazine ring-containing cyclic ethylenamines is small. Namely, it is possible to obtain ethylenamines having high non cyclic rates and industrially preferred quality. This process is practically widely used. However, it has a problem that a large amount of sodium chloride is formed as a by-product, and its separation and treatment are costly.

Another process wherein a monoethanolamine is used as starting material, and ammonia is reacted thereto in the presence of hydrogen and a hydrogenation catalyst to obtain an ethylenamine, is also widely practically employed. However, according to this process, piperazine ring containing cyclic ethylenamines which are undesirable from the viewpoint of quality, are likely to be produced in a substantial amount although ethylenediamines may be produced with high efficiency. Therefore, it is difficult to produce polyethylenepolyamines having high molecular weights.

In addition to these processes, a process has been proposed wherein monoethanolamine is used as starting material, and ammonia or/and ethylenamine are reacted thereto by using a phosphorus-containing substance as catalyst to produce an ethylenamine. For example, Japanese Unexamined Patent Publication No. 147600/1976 discloses a process wherein phosphoric acid or phosphorous acid is used as catalyst. However, these catalysts are soluble in the reaction solution containing water. Therefore, a special step for the separation and recovery from the reaction solution is required. Under the circumstances, processes for the production of ethylenamines have been proposed wherein various salts of phosphoric acid and supported phosphoric acid insoluble in the reaction solution containing water are used as catalysts. U.S. Pat. No. 4,448,997 discloses a process for producing ethylenamines wherein aluminum phosphate is used as catalyst, and Japanese Unexamined Patent Publication No. 41641/1985 discloses such a process wherein a phosphate of a metal of Group IIIb such as lanthanum phosphate is used as catalyst. Further, Japanese Unexamined Patent Publication No. 150538/1984 discloses a process wherein phosphoric acid supported on e.g. titanium dioxide is used as catalyst. However, these phosphates and supported phosphoric acid are substantially poorer in the catalytic activities than free phosphoric acid. Further, by the use of these phosphoric acid type catalysts, it is not possible to reduce piperazine ring-containing cyclic amines undesirable from the viewpoint of quality to a level sufficiently low for the industrial purpose. As a phosphorous-containing catalyst having high activities, there is a phosphorus-containing ion exchanger resin. However, this catalyst is poor in the heat resistance and thus has a problem in the catalytically useful life.

As a non-phosphorus catalyst, silica or alumina is disclosed in Japanese Unexamined Patent Publication No. 38329/1980, but the catalytic activities of this catalyst are very low.

As described above, many processes have been disclosed for the production of polyalkylene polyamines. However, such processes are still inadequate from the industrial point of view. Particularly it is desired to develop a process for producing high quality polyalkylene polyamines having high non-cyclic rates by using a solid catalyst having high catalytic activities and high heat resistance and being hardly soluble in the reaction solution, for the production of polyalkylene polyamines using alkanolamines as starting material.

Under these circumstances, the present inventors have conducted extensive researches on a process for producing polyalkylene polyamines having alkylene chains increased over ammonia and/or alkylenamines used as starting material by the reaction of the ammonia and/or alkylenamines with alkanolamines. As a result, they have found that a catalyst having a niobium-containing substance, such as niobium pentoxide or a niobate, supported on a carrier, has high activities as catalyst and is a solid hardly soluble in a reaction solution containing water, and it is also excellent in the heat resistance. The present invention has been accomplished on the basis of these discoveries.

The present invention provides a process for producing polyalkylene polyamines, which comprises reacting ammonia and/or an alkylenamine with an alkanolamine to obtain an alkylenamine having an increased number of alkylene chains over the ammonia and/or the alkylenamine as starting material, wherein a catalyst having a niobium-containing substance supported on a carrier is used for the reaction.

Now, the present invention will be described in further detail.

The catalyst used in the process of the present invention is a catalyst having a niobium-containing substance supported on a carrier.

In the process of the present invention, "supported on a carrier" means that a carrier in a solid state and a substance to be supported in a non-solid state are brought in contact with each other to provide an interaction. After the contact with the carrier, the supported substance may be in a solid state or in a liquid state. Further, the interaction between the carrier and the supported substance may be a physical interaction or a chemical interaction.

In the process of the present invention, the carrier may be any material so long as it is capable of having an interaction with the supported substance. For example, it may be a metal oxide such as silica, titania, alumina, zirconia, magnesia or calcia, a mixed oxide such as silica-alumina or silica titania, active carbon, or porous vycor glass. The carrier may be in the form of a powder or a molded product. The carrier usually has a surface area of at least 0.1 m$^2$/g, preferably at least 1 m$^2$/g. If the surface area of the carrier is less than 0.1 m$^2$/g, the heat resistance of the catalyst tends to be low, and the amount of the supported substance tends to be small.

The supported substance in the process of the present invention is a niobium-containing substance. The niobium-containing substance means a substance wherein niobium and other elements are chemically bonded, and there is no particular restriction so long as it is a substance containing niobium. Specifically, it may be a niobium oxide such as niobium pentoxide, niobium tetroxide, niobium trioxide, niobium dioxide or niobium monoxide, a niobate such as lithium niobate, sodium niobate, magnesium niobate, aluminum niobate, potassium niobate, calcium niobate, manganese niobate, iron niobate, rubidium niobate, yttrium niobate, silver niobate, cesium niobate, barium niobate or mercury niobate, a fluoroniobate such as sodium fluoroniobate or potassium fluoroniobate, niobium fluoride such as niobium pentafluoride or niobium trifluoride, a niobium chloride such as niobium pentachloride, niobium tetrachloride or niobium trichloride, a niobium bromide such as niobium pentabromide, niobium tetrabromide or niobium tribromide, a niobium iodide such as niobium pentiodide, niobium tetriodide or niobium triiodide, a niobium oxyhalide such as niobium oxyfluoride, niobium oxychloride, niobium oxybromide or niobium oxyiodide, a niobium alkoxide such as niobium methoxide, niobium ethoxide, niobium propoxide, niobium isopropoxide, niobium butoxide, niobium isobutoxide, niobium pentyloxide or niobium phenoxide, or an organic acid salt of niobium such as niobium oxalate. As the niobium-containing substance in the process of the present invention, preferred is a substance wherein pentavalent niobium and other elements are chemically bonded. A niobium oxide or a niobate is further preferred.

In the process of the present invention, a pentavalent niobium oxide and a pentavalent niobate may be used alone or in combination as a mixture thereof.

The amount of the niobium-containing substance in the catalyst used in the process of the present invention, varies substantially depending upon the carrier or the substance to be supported thereon, and can not easily be defined. However, in the case where the niobium-containing substance is niobium oxide, the amount of niobium oxide in the entire catalyst is usually at last 0.001% by weight and less than 70% by weight, preferably at least 0.01% by weight and less than 50% by weight. If the amount is less than 0.001% by weight, the activities tend to be low, and if it is 70% by weight or more, the heat resistance tends to be low.

There is no particular restriction as to the method for the preparation of the catalyst having a niobium-containing substance supported on a carrier, to be used in the process of the present invention. For example, various methods are available to support niobium pentoxide, including 1) a method wherein niobium pentoxide is dissolved in an acid such as sulfuric acid and impregnated into a carrier, followed by the contact with a basic substance, and 2) a method wherein a niobium alkoxide, an organic acid salt of niobium or a niobate is contacted with a carrier, followed by the thermal decomposition or hydrolysis to convert it to niobium oxide. Any one of such methods may be employed.

In the process of the present invention, there is no particular restriction as to the shape of the catalyst. The catalyst supported on a molded product may be used as it is. The catalyst supported on a powder may be used as it is in the form of the powder, or after being molded. For example, in a suspended bed system, it is used in a powder or granular form. In a fixed bed system, it is used in a molded form of pellets or beads.

The molding method of the catalyst includes extrusion molding, tablet molding or granule molding. For the molding, silica, alumina, alumina-silica, clay or the like may be added as a binder.

The catalyst may be used after calcination or without calcination. When calcination is applied, there is no particular restriction as to the calcination temperature. However, the calcination temperature is preferably not higher than 800° C. If calcination is conducted at a temperature exceeding 800° C., the surface area tends to be small, whereby the catalytic activities tend to be reduced.

The amount of the catalyst used in the present invention may be at any level so long as it is sufficient to have the reaction proceeded at an industrially useful reaction rate. The amount varies to a large extent depending upon the reaction system i.e. whether it is a suspension bed system or a fixed bed system, and upon the carrier used and the substance supported thereon, and it can not generally be defined. However, for example, in a suspension bed system, the catalyst is used usually in an amount of from 0.05 to 50% by weight based on the total weight of the starting materials. If the amount is less than 0.05% by weight, no adequate reaction rate is obtainable, and if it exceeds 50% by weight, no sufficient effects corresponding to the amount will be obtained.

The starting materials used for the process of the present invention, are ammonia, an alkylenamine and an alkanolamine.

Ammonia or the alkylenamine to be used in the process of the present invention is a compound represented by the formula I:

(I)

wherein a is a number of from 2 to 6, r is a number of from 0 to 6, $R_1$ is hydrogen or an alkyl group having from 1 to 4 carbon atoms, $R_1'$ is a group represented by the formula (1):

(1)

wherein b is a number of from 1 to 6, d is 0 or 1, and s is a number of from 0 to 4, or a compound represented by the formula II:

(II)

wherein e is a number of from 2 to 6, f is a number of from 2 to 6, and each of $R_2$ and $R_2'$ is a group represented by the formula (2):

(2)

wherein g is a number of from 2 to 6, and t is a number of 0 to 5.

Either the compound of the formula I or the compound of the formula II may be employed. Preferably, however, ammonia or an alkylenamine of the formula I is employed. When an alkylenamine of the formula I is used, a high quality polyalkylene polyamine having a high non-cyclic rate is obtainable. Ammonia and the alkylenamine of the formula I include ammonia, ethylenamines such as ethylenediamine, diethylenetriamine, triethylenetetramine, tetraethylenepentamine, pentaethylenehexamine and hexaethyleneheptamine, propyleneamines such as propylenediamine and dipropylenetriamine, butyleneamines such as butylenediamine and dibutylenetriamine, alkylenamines such as hexamethylenediamine and alkylated products thereof such as N-methylethylenediamine and N-ethylethylenediamine. Among them ethylenamines such as ethylenediamine and diethylenetriamine are preferred as starting material to be used in the process of the present invention.

Ammonia and alkylenamines to be used in the process of the present invention may be used alone or in combination as a mixture of two or more different kinds.

The alkanolamine to be used in the process of the present invention is a compound represented by the formula III:

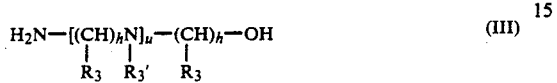

wherein h is a number of from 2 to 6, u is a number of from 0 to 5, $R_3$ is hydrogen or an alkyl group having from 1 to 4 carbon atoms, and $R_3'$ is a group represented by the formula (3):

wherein i is a number of from 1 to 6, j is 0 or 1, and v is a number of from 0 to 4, or a compound represented by the formula IV:

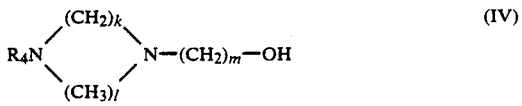

wherein k is a number of from 2 to 6, l is a number of from 2 to 6, m is a number of from 2 to 6, and $R_4$ is a group represented by the formula (4):

wherein n is a number of from 2 to 6, and w is a number of from 0 to 5.

Either the compound of the formula III or the compound of the formula IV may be employed. However, the alkanolamine of the formula III is preferably employed. When the alkanolamine of the formula III is used, a high quality alkylenamine having a high non-cyclic rate is obtainable. The alkanolamine of the formula III includes alkanolamines such as monoethanolamine, N-(2-aminoethyl)ethanolamine, 3-amino-1-propanol and N-(3-aminopropyl)propanolamine. As the starting material to be used in the process of the present invention, ethanolamines such as monoethanolamine and N (2-aminoethyl)ethanolamine are preferred.

The alkanolamines to be used in the process of the present invention may be used alone or in combination as a mixture of two or more different kinds.

The combination of starting materials supplied for the reaction in the process of the present invention includes the following three types:
1) Ammonia and an alkanolamine;
2) An alkylenamine and an alkanolamine; and
3) Ammonia, an alkylenamine and an alkanolamine.
The reaction may be conducted by any one of such combinations. Preferred combinations of starting materials include:
1) Ammonia and an alkanolamine of the formula III;
2) An alkylenamine of the formula I other than ammonia and an alkanolamine of the formula III; and
3) Ammonia and an alkylenamine of the formula I and an alkanolamine of the formula III. More preferred combinations of starting materials include:
1) Ammonia and an ethanolamine;
2) An ethylenamine and an ethanolamine; and
3) Ammonia, an ethylenamine and an ethanolamine.

Preferred molar ratios of the starting materials to be supplied in the process of the present invention are as follows:
1) In a case where ammonia and an alkanolamine are used as starting materials, the molar ratio of ammonia/the alkanolamine is from 2 to 30;
2) In a case where an alkylenamine and an alkanolamine are used as starting materials, the molar ratio of the alkylenamine/the alkanolamine is from 0.5 to 10; and
3) In a case where ammonia, an alkylenamine and an alkanolamine are used as starting materials, the molar ratio of (ammonia +the alkylenamine)/the alkanolamine is from 0.5 to 30.

In each case, the quality of the resulting polyalkylene polyamine varies depending upon the molar ratio of the starting materials. If the molar ratio is smaller than the above-mentioned ranges, piperazine ring-containing amines will be produced in a substantial amount, whereby polyalkylene polyamines having undesirable quality tend to form. If the molar ratio is larger than the above range, the reaction rate tends to decrease, and the pressure is required to be extremely high, such being not practical.

In the process of the present invention, the resulting polyalkylene polyamine differs depending upon the types of the starting materials. When an alkanolamine is reacted to ammonia and/or an alkylenamine, the resulting alkylenamine has alkylene chains increased over the ammonia or the alkylenamine as starting material. Namely, when the alkanolamine of the formula III is reacted to the ammonia and/or the alkylenamine of the formula I, the resulting polyalkylene polyamine will be a compound represented by the formula V:

wherein o is a number of from 2 to 6, x is a number of 1 to 7, $R_5$ is hydrogen or an alkyl group having from 1 to 4 carbon atoms, and $R_5'$ is a group of the formula (5):

wherein p is a number of from 1 to 6, q is 0 or 1, and y is a number of 0 to 4, wherein x and/or y in the resulting polyalkylene polyamine is a number larger at least by one than r and/or s of the ammonia or the alkylenamine as starting material of the formulas (I) and (1). Thus, a polyalkylene polyamine having an increased number of alkylene chains over the starting material is obtainable. For example, when ammonia is reacted with monoethanolamine, ethylenediamine and non cyclic polyethylenepolyamines such as diethylenetriamine, triethylenetetramine, tetraethylenepentamine and pentaethylenehexamine will be formed. When ethylenediamine is reacted with monoethanolamine, the above-mentioned non-cyclic polyethylenepolyamines will be formed. When ammonia and ethylenediamine are reacted with monoethanolamine, ethylenediamine and the above-mentioned non-cyclic polyethylenepolyamines will be formed.

In the process of the present invention, the reaction is conducted usually at a temperature within a range of from 200° to 400° C., preferably from 240° to 350° C. If the temperature is less than 200° C., the reaction rate tends to be substantially low, and if it exceeds 400° C., the resulting polyalkylene polyamine tends to undergo decomposition, such being undesirable.

In the process of the present invention, the reaction may be conducted in a gas phase or in a liquid phase. However, it is preferred to conduct it in a liquid phase in order to produce a high quality polyalkylene polyamine.

In the process of the present invention, the reaction may be conducted by a suspended batch, semi-batch or continuous system, or by a fixed bed system. However, the fixed bed system is industrially advantageous from the viewpoint of the operation, apparatus and economy.

In the process of the present invention, the pressure for the reaction varies substantially depending upon whether the reaction is a gas phase reaction or a liquid phase reaction, or whether or not ammonia is used. Therefore, it is difficult to define the pressure range. However, for example, in the case of a liquid phase reaction using no ammonia, the pressure is within a range of from about 1 to 300 kg/cm$^2$G.

In the process of the present invention, the catalyst is separated and recovered from the reaction solution in a usual manner, and then the starting material is separated and recovered by distillation. The separated and recovered starting material may be recycled to the reaction zone, as the case requires. A part of the reaction product may be recycled to the reaction zone in order to change the composition of the reaction product. The separation of the starting material and the product is usually conducted by distillation. Such distillation may be conducted by a continuous system or by a batch system.

The reaction product may be treated with active carbon or sodium borohydride in order to improve the purity or color tone of the reaction product. The color tone, odor, etc. of the reaction product may be improved by conducting the reaction in the presence of hydrogen.

The formed water may be removed from the reaction zone in order to reduce the formation of amines undesirable from the viewpoint of quality such as hydroxyl group-containing amines or to improve the reaction rate. Otherwise, the reaction may be conducted with an addition of water in order to prolong the useful life of catalyst or to make it easy to handle ammonia or the alkylenamine.

The present invention provides a process for producing a high quality polyalkylene polyamine in good yield by using a niobium-containing substance supported on a carrier, as catalyst, which is highly active, resistant to corrosion by the reaction solution and excellent in the heat resistance, and thus it is industrially extremely significant.

Now, the present invention will be described in further detail with reference to Examples. However, it should be understood that the present invention is by no means restricted to such specific Examples.

Polyalkylene polyamines as reaction products and alkylenamines and alkanolamines as starting materials will be represented by the following abbreviations:

EDA: Ethylenediamine
MEA: Monoethanolamine
PIP: Piperazine
AEP: N-(2-aminoethyl)piperazine
DETA: Diethylenetriamine
AEEA: N-(2-aminoethyl)ethanolamine
TETA: Triethylenetetramine (linear, branched or cyclic isomer)
TEPA: Tetraethylenepentamine (linear, branched or cyclic isomer)
NH$_3$: Ammonia EXAMPLE 1: Preparation of catalysts

CATALYST 1

5 g of niobium pentachloride was dissolved in 25 ml of methanol. To this solution, 10 g of silica powder (pulverized product of N-608, manufactured by Nikki Kagaku K. K..) was added as carrier. The solvent was distilled off at 40° C. under reduced pressure. 50 ml of water was added to the residue, followed by refluxing for one hour. The product was collected by filtration, washed with air and calcined at 400° C. for 2 hours under a dry air stream to obtain Catalyst 1. The amount of niobium oxide supported in Catalyst 1 was 20% by weight, and the BET specific surface area was 152 m$^2$/g.

100 ml of water was added to 1 g of Catalyst 1, followed by refluxing for 2 hours. Then, the catalyst was collected by filtration and calcined at 400° C. for 2 hours under a dry air stream, whereby Catalyst 1 was recovered 100%.

CATALYST 2

Catalyst 2 was prepared in the same manner as for the preparation of Catalyst 1 except that the amount of silica powder as carrier was changed to 25 g. The amount of niobium oxide supported in Catalyst 2 was 9% by weight, and the BET specific surface area was 131 m$^2$/g.

CATALYST 3

Catalyst 3 was prepared in the same manner as for the preparation of Catalyst 1 except that 10 g of alumina powder (pulverized product of KHA-24, manufactured by Sumitomo Kagaku K. K.) was used as carrier. The amount of niobium oxide supported in Catalyst 3 was 20% by weight, and the BET specific surface area was 192 m$^2$/g.

CATALYST 4

Catalyst 4 was prepared in the same manner as for the preparation of Catalyst 1 except that the amount of alumina powder as carrier was changed to 25 g. The amount of niobium oxide supported in Catalyst 4 was 9% by weight, and the BET specific surface area was 182 m$^2$/g.

CATALYST 5

Catalyst 5 was prepared in the same manner as for the preparation of Catalyst 1 except that 10 g of titania powder (anatase type) was used as carrier. The amount of niobium oxide supported in Catalyst 5 was 20% by weight, and the BET specific surface area was 72 m$^2$/g.

CATALYST 6

Catalyst 6 was prepared in the same manner as for the preparation of Catalyst 1 except that 25 g of titania powder was used as carrier. The amount of niobium oxide supported in Catalyst 6 was 9% by weight, and the BET specific surface area was 35 m$^2$/g.

CATALYST 7

Catalyst 7 was prepared in the same manner as for the preparation of Catalyst 1 except that 10 g of light magnesia powder was used as carrier. The amount of niobium oxide supported in Catalyst 7 was 20% by weight, and the BET specific surface area was 75 m$^2$/g.

CATALYST 8

Catalyst 8 was prepared in the same manner as for the preparation of Catalyst 1 except that 10 g of silica-alumina powder (pulverized product of Neobead SA-5, manufactured by Mizusawa Kagaku K. K.) was used as carrier. The amount of niobium oxide supported in Catalyst 8 was 20% by weight, and the BET specific surface area was 385 m$^2$/g.

CATALYST 9

In 30 ml of acetic acid, 8.0 g of niobium pentaethoxide was dissolved. To this solution, 30 g of amorphous titania powder was added. Then, acetic acid was distilled off under reduced pressure. To the residue, 100 ml of water was added, followed by refluxing for one hour. The product was collected by filtration, washed with water and calcined at 400° C. for 2 hours under a dry air stream to obtain Catalyst 9. The amount of the niobium-containing substance supported in Catalyst 9 was 10% by weight, and the BET specific surface area was 113 m$^2$/g.

CATALYST 10

Catalyst 9 was calcined at 600° C. for 2 hours under a dry ar stream to obtain Catalyst 10. The BET specific surface area of Catalyst 10 was 100 m$^2$/g.

CATALYST 11

Catalyst 11 was prepared in the same manner as for the preparation of Catalyst 9 except that 23.9 g of niobium pentaethoxide was used. The amount of the niobium-containing substance supported in Catalyst 11 was 2596 5% by weight, and the BET specific surface area was 139 m$^2$/g.

CATALYST 12

Catalyst 11 was calcined at 600° C. for 2 hours under a dry air stream to obtain Catalyst 12. The BET specific surface area of Catalyst 12 was 100 m$^2$/g.

CATALYST 13

5 g of niobium pentaethoxide was added to 100 ml of n-hexane, and 10 g of silica powder (puverized product of N-608 manufactured by Nikki Kagaku K. K.) was added as carrier, followed by refluxing for 2 hours under a nitrogen stream. The product was collected by filtration and washed with n-hexane. To this washed product, 100 ml of water was added, followed by refluxing for 2 hours. Then, the product was calcined at 400° C. for 2 hours under a dry air stream to obtain Catalyst 13. The amount of the niobium-containing substance supported in Catalyst 13 was 12.7% by weight.

CATALYST 14

35.83 g of niobium pentaethoxide was dissolved in 1 l of n hexane under a nitrogen stream. To this solution, 130 g of amorphous titania powder was added, followed by refluxing for 3 hours. The product was collected by filtration and washed with 500 ml of ethanol and 500 ml of n-hexane. To this washed product, 500 ml of water was added, followed by refluxing for 2 hours. The product was calcined at 400° C. for 2 hours under a dry air stream. To this product, water was added, followed by drying at 120° C. 95.21 g of the supported catalyst thus obtained was put into 300 ml of a n-hexane solution having 15 g of niobium pentaethoxide dissolved therein, followed by refluxing for 3 hours under a nitrogen stream. The product was washed with n-hexane and ethanol, and 300 ml of water was added, followed by refluxing for 2 hours. The product was calcined at 400° C. for 2 hours under a dry air stream.

To the calcined product, water was added, followed by drying at 120° C. 81.42 g of the supported catalyst thus obtained, was put into 300 ml of a n-hexane solution having 15 g of niobium pentaethoxide dissolved therein, followed by refluxing for 3 hours under a nitrogen stream. The product was washed with n-hexane and ethanol, and 300 ml of water was added thereto, followed by refluxing for 2 hours. The product was calcined at 400° C. for 2 hours under a dry air stream to obtain Catalyst 14. The amount of the niobium-containing substance supported in Catalyst 14 was 15.67% by weight, and the BET specific surface area was 107 m$^2$/g.

CATALYST 15

Catalyst 14 was calcined at 600° C. for 2 hours under a dry air stream to obtain Catalyst 15. The BET specific surface area of Catalyst 15 was 93 m$^2$/g.

CATALYSTS 16 to 30

Niobium oxide and oxalic acid dihydrate were dissolved in water at 110° C. Then, the solution was cooled with ice, and the precipitated oxalic acid was removed by filtration. The filtrate was concentrated. The carriers as identified in Table 1 were impregnated with this concentrated solution. Then, they were dried and calcined at 600° C. for 2 hours under a dry air stream to obtain catalysts as identified in Table 1.

TABLE 1

| Catalyst No. | Carrier | | | Amount of supported niobium oxide (wt %) |
|---|---|---|---|---|
| 16 | Alumina | 5 mmΦ × 5 mm cylindrical | manufactured by Nikki Kagaku K.K. | 12.1 |
| 17 | Alumina | 3 mmΦ spherical | manufactured by Sumitomo Kagaku K.K. | 20.7 |
| 18 | Alumina | 3 mmΦ spherical | manufactured by Sumitomo Kagaku K.K. | 5.5 |
| 19 | Alumina | 3 mmΦ spherical | manufactured by Sumitomo Kagaku K.K. | 0.5 |
| 20 | Alumina | 5 mmΦ spherical | manufactured by Norton Company | 11.7 |
| 21 | Silica | 5 mmΦ × 5 mm cyclindrical | manufactured by | 8.5 |

TABLE 1-continued

| Catalyst No. | | Carrier | | Amount of supported niobium oxide (wt %) |
|---|---|---|---|---|
| 22 | Silica | 3 mmΦ × 3 mm cyclindrical | manufactured by Nikki Kagaku K.K. | 7.7 |
| 23 | Silica | 3 mmΦ spherical | manufactured by Nikki Kagaku K.K. | 14.8 |
| 24 | Silica | 3 mmΦ spherical | manufactured by Fuji Devison Co. | 19.7 |
| 25 | Silica-alumina | 3 mmΦ spherical | manufactured by Fuji Devison Co. | 10.4 |
| 26 | Silica-titania | 5 mmΦ × 5 mm cylindrical | manufactured by Mizusawa Kagaku K.K. | 4.8 |
| 27 | Titania | 5 mmΦ × 5 mm cylindrical | manufactured by Nikki Kagaku K.K. | 8.9 |
| 28 | Titania | 5 mmΦ × 5 mm cylindrical | manufactured by Nikki Kagaku K.K. | 9.3 |
| 29 | Titania | 5 mmΦ × 3 mm cylindrical | Tabletted product | 8.6 |
| 30 | Zirconia | 5 mmΦ × 3 mm cylindrical | Tabletted product | 26.0 |

COMPARATIVE CATALYST A 130 g of lanthanum nitrate hexahydrate was dissolved in deionized water under stirring. 79.2 g of diammonium hydrogenphosphate was dissolved in deionized water under stirring. While vigorously stirring the aqueous diammonium hydrogenphosphate solution, the aqueous lanthanum nitrate solution was added at once, whereby thick bulky precipitates formed. A thick creamy suspension formed by stirring, was subjected to filtration under suction to separate precipitates. The paste-like solid thus obtained was thoroughly washed with deionized water and then dried at a temperature of from 80° to 90° C. to obtain Comparative Catalyst A.

COMPARATIVE CATALYST B

Niobium oxide (manufactured by CBMM Company) was calcined at 400° C. for 2 hours under a dry air stream. The BET specific surface area of the calcined product was 99 m²/g. This product was further calcined at 600° C. for 2 hours under a dry air stream to obtain Comparative Catalyst B. The BET specific surface area of Comparative Catalyst B was 12 m²/g.

EXAMPLE 2

Into a 200 ml stainless steel autoclave equipped with an electromagnetic stirrer, 60 g of EDA, 30 g of MEA and 3 g of Catalyst 1 were charged. After flushing with nitrogen, the mixture was heated to 300° C. and maintained at that temperature for 5 hours. The reaction pressure was 36.0 kg/cm²G. Then, the reaction solution was cooled and analyzed by gas chromatography. The conversion of MEA was 46.6%, and the composition of the reaction product excluding the starting materials and formed water was as follows: PIP: 3.46% by weight, DETA: 41.13% by weight, AEEA: 7.21% by weight, AEP: 1.86% by weight, and TETA: 11.05% by weight. The recovery rate of Catalyst 1 was 100%.

EXAMPLE 3

The reaction was conducted under the same condition as in Example 2 except that the reaction was conducted for 3 hours by using 3.0 g of Catalyst 11. The results are shown in Table 2.

COMPARATIVE EXAMPLE 1

The reaction was conducted under the same condition as in Example 2 except that the reaction was conducted for 3.0 hours by using 3.0 g of Comparative Catalyst A. The results are shown in Table 2.

COMPARATIVE EXAMPLE 2

The reaction was conducted under the same condition as in Example 2 except that the reaction was conducted for 6.3 hours by using 12 g of silica powder (manufactured by Nikki Kagaku K. K.) as catalyst. The results are shown in Table 2.

TABLE 2

| | Conversion of MEA (%) | Non-cyclic TETA (%)* |
|---|---|---|
| Example 3 | 47.5 | 91.8 |
| Comparative Example 1 | 26.8 | 89.4 |
| Comparative Example 2 | 28.8 | 88.4 |

*Gas chromatogram area %: (Branched + linear)/(Branched + linear + cyclic isomer) × 100

EXAMPLE 4

The reaction was conducted under the same condition as in Example 2 except that 4 g of Catalyst 12 was used as the catalyst, and the reaction was conducted for 5 hours. As a result, the conversion of MEA was 54.6%, and the composition of the reaction product excluding the starting materials and formed water was as follows: PIP: 0.80% by weight, DETA: 8.64% by weight, AEEA: 1.50% by weight, AEP: 0.30% by weight, TETA: 2.14% by weight, and TEPA: 0.05% by weight.

COMPARATIVE EXAMPLE 3

The reaction was conducted under the same condition as in Example 4 except that Comparative Catalyst B was used as the catalyst. As a result, the conversion of MEA was 12.1%, and little ethylenamines formed.

EXAMPLES 5 to 16

The reactions were conducted under the same condition as in Example 2 except that as the catalyst, those identified in Table 3 were used in the amount as identified in Table 3, and the reactions were conducted for the periods of time as identified in Table 3. The results are shown in Table 3.

TABLE 3

| Example No. | Catalyst No. | Amount of catalyst (g) | Time (hr) | Conversion of MEA (%) |
|---|---|---|---|---|
| 5 | 2 | 11.2 | 5 | 62.4 |
| 6 | 3 | 4.5 | 5 | 58.4 |
| 7 | 4 | 11.2 | 5 | 56.1 |
| 8 | 5 | 3.0 | 5 | 38.6 |
| 9 | 6 | 11.2 | 5 | 55.6 |
| 10 | 7 | 4.5 | 5 | 14.1 |
| 11 | 8 | 4.5 | 5 | 52.6 |
| 12 | 9 | 10.0 | 3 | 55.5 |
| 13 | 10 | 10.0 | 3 | 55.0 |
| 14 | 13 | 3.0 | 3 | 36.2 |
| 15 | 14 | 3.0 | 5 | 46.3 |
| 16 | 15 | 3.0 | 5 | 42.0 |

EXAMPLE 17

Into a 200 ml stainless steel autoclave equipped with an electromagnetic stirrer, 50 g of EDA, 25 g of MEA and 7 g of Catalyst 11 were charged. After flushing with nitrogen, 41 g of ammonia was added thereto. The mixture was heated to 280° C. and maintained at that temperature for one hour. The reaction pressure was 238 kg/cm$^2$G. After cooling, the reaction solution was taken out and analyzed by gas chromatography. As a result of the analysis, the conversion of MEA was 45.2%, and the composition of the reaction product excluding the starting materials and formed water was as follows: PIP: 2.55% by weight, DETA: 38.23% by weight, AEEA: 3.51% by weight, AEP: 1.80% by weight, and TETA: 11.25% by weight.

EXAMPLE 18

Into a stainless steel autoclave equipped with an electromagnetic stirrer, 60 g of EDA and 30 g of MEA were charged. Further, a stainless steel basket was attached to a stirring shaft, and 3 g of Catalyst 16 was put in the basket. After flushing with nitrogen, the mixture was heated to 300° C. and maintained at that temperature for 5 hours. After cooling, the reaction solution was taken out and analyzed by gas chromatography. As a result, the conversion of MEA was 54.1%, and the composition of the reaction product excluding the starting materials and formed water was as follows: PIP: 2.97% by weight, DETA: 41.33% by weight, AEEA: 4.80% by weight, AEP: 1.98% by weight, TETA: 18.17% by weight, and TEPA: 4.34% by weight. Further, the TETA non-cyclic rate was 90.44%.

COMPARATIVE EXAMPLE 4

The reaction was conducted under the same condition as in Example 18 except that 3 g of the same alumina molded product as used in Catalyst 16, was used as the catalyst. As a result, the conversion of MEA was 23.0%, and the composition of the reaction product excluding the starting materials and formed water was as follows: PIP: 6.19% by weight, DETA: 17.04% by weight, AEEA: 8.12% by weight, and AEP: 0.80% by weight. No formation of TETA was observed.

EXAMPLE 19

The reaction was conducted under the same condition as in Example 18 except that Catalyst 23 was used as the catalyst. As a result, the conversion of MEA was 52.6%, and the composition of the reaction product excluding the starting materials and formed water was as follows: PIP: 3.57% by weight, DETA: 41.50% by weight, AEEA: 9.87% by weight, AEP: 1.98% by weight, TETA: 14.74% by weight, and TEPA: 3.53% by weight. Further, the TETA non-cyclic rate was 88.24%.

COMPARATIVE EXAMPLE 5

The reaction was conducted under the same condition as in Example 18 except that the same silica molded product as used in Catalyst 23, was used as the catalyst. As a result, the conversion of MEA was 11.9%, and little ethylenamines formed.

EXAMPLES 20 TO 31

The reactions were conducted under the same condition as in Example 18 except that 3 g of the catalysts identified in Table 4 were used as a catalyst. The results are shown in Table 4.

TABLE 4

| Example No. | Catalyst No. | Conversion of MEA (%) | Non-cyclic TETA (%) |
|---|---|---|---|
| 20 | 18 | 45.6 | 90.33 |
| 21 | 19 | 32.2 | 85.14 |
| 22 | 20 | 32.6 | 93.21 |
| 23 | 21 | 39.0 | 85.06 |
| 24 | 22 | 28.3 | TETA not formed |
| 25 | 24 | 52.3 | 88.30 |
| 26 | 25 | 31.3 | TETA not formed |
| 27 | 26 | 33.0 | TETA not formed |
| 28 | 27 | 43.8 | TETA not formed |
| 29 | 28 | 43.2 | 82.57 |
| 30 | 29 | 41.9 | 86.09 |
| 31 | 30 | 42.3 | 81.52 |

EXAMPLES 32 to 34

Into a stainless steel autoclave equipped with an electromagnetic stirrer, 60 g of EDA, 30 g of MEA and Catalyst 17 in the amount as identified in Table 5, were charged and the reaction was conducted at the reaction temperature as identified in Table 5 for a period of time as identified in Table 5. The results are shown in Table 5.

TABLE 5

| Example No. | Amount of catalyst (g) | Reaction time (h) | Reaction temp. (°C.) | Conversion of MEA (%) |
|---|---|---|---|---|
| 32 | 3 | 1 | 320 | 55.7 |
| 33 | 6 | 5 | 280 | 34.2 |
| 34 | 9 | 10 | 250 | 14.3 |

EXAMPLES 35 to 37

Into a 200 ml stainless steel autoclave equipped with an electromagnetic stirrer, the starting materials as identified in Table 6, and 3 g of Catalyst 17 were charged and reacted at 300° C. for 4 hours. The results are shown in Table 6.

TABLE 6

| Example No. | Starting materials (g) EDA | Starting materials (g) MEA | Conversion of MEA (%) | Non-cyclic TETA (%) |
|---|---|---|---|---|
| 35 | 30 | 60 | 53.2 | 66.29 |
| 36 | 45 | 45 | 51.8 | 87.44 |
| 37 | 72 | 18 | 52.5 | 94.82 |

EXAMPLE 38

Into a 200 ml stainless steel autoclave equipped with an electromagnetic stirrer, 60 g of DETA, 30 g of AEEA and 3 g of Catalyst 17, and the mixture was reacted at 300° C. for 4 hours. As a result, the conversion of AEEA was 91.7%, and the composition of the product solution excluding the starting materials and formed water was as follows: PIP: 11.55% by weight, TETA: 17.88% by weight, and TEPA: 24.95% by weight.

We claim:

1. A process for preparing a polyalkylene polyamine having an increased number of alkylene units from a starting material selected from the group consisting of ammonia and alkylenamines and wherein the alkylenamine starting material is selected from the group consisting of:

compounds represented by the following formula:

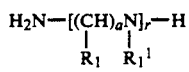

wherein a is a number from 2 to 6, r is a number from 0 to 6, $R_1$ represents a hydrogen atom or an alkyl group having 1 to 4 carbon atoms, and $R_1^1$ represents a group represented by the following formula:

wherein b is a number from 1 to 6, d is 0 or 1, and s is a number from 0 to 4 and further wherein the starting material is reacted with an alkanolamine in the presence of a catalyst having a niobium-containing substance supported on a carrier which catalyst on a carrier has been calcined at a temperature of 400° C. to 800° C.

2. The process according to claim 1, wherein the niobium-containing substance is niobium pentoxide or a niobate.

3. The process according to claim 1, wherein the carrier is alumina, silica, titania, zirconia, silica-alumina, silica-titania or magnesia.

4. The process according to claim 1, wherein the alkylenamine as starting material is an ethylenamine.

5. The process according to claim 1, wherein the alkanolamine is an ethanolamine.

6. The process according to claim 1, wherein the alkanolamine is selected from the group consisting of compounds represented by the following formula:

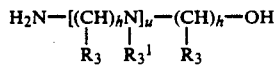

wherein h is a number of from 2 to 6, u is a number of from 1 to 5, $R_3$ is hydrogen or an alkyl group having from 1 to 4 carbon atoms, and $R_3^1$ is a group of the formula:

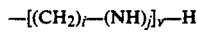

wherein i is a number of from 1 to 6, j is 0 or 1, and v is a number of from 0 to 4.

7. The process according to claim 1 wherein the reaction is carried out in a liquid phase.

* * * * *